United States Patent
Darnell

(10) Patent No.: US 8,100,693 B2
(45) Date of Patent: Jan. 24, 2012

(54) CUSTOM FIT DENTAL TRAY AND METHOD FOR MAKING SAME

(76) Inventor: Daniel Henry Darnell, Cullman, AL (US)

(*) Notice: Subject to any disclaimer, the term of this patent is extended or adjusted under 35 U.S.C. 154(b) by 506 days.

(21) Appl. No.: 12/383,321

(22) Filed: Mar. 23, 2009

(65) Prior Publication Data

US 2009/0239190 A1    Sep. 24, 2009

Related U.S. Application Data

(60) Provisional application No. 61/070,390, filed on Mar. 21, 2008, provisional application No. 61/123,123, filed on Apr. 4, 2008, provisional application No. 61/099,235, filed on Sep. 23, 2008.

(51) Int. Cl.
*A61C 9/00* (2006.01)

(52) U.S. Cl. ............ 433/214; 433/37; 433/48; 433/215; 425/2

(58) Field of Classification Search .................. 433/34, 433/37, 38, 45, 47, 48, 71, 140, 214, 215; 425/2, 89; 128/861, 862; 264/16–20; 523/109
See application file for complete search history.

(56) References Cited

U.S. PATENT DOCUMENTS

| | | | | |
|---|---|---|---|---|
| 1,470,826 A * | 10/1923 | Gambill | ........................ | 425/175 |
| 1,663,695 A * | 3/1928 | Foster, Jr. | ........................ | 433/48 |
| 2,598,927 A * | 6/1952 | May | ........................ | 433/47 |
| 2,682,725 A * | 7/1954 | Atwood | ........................ | 211/42 |
| 3,056,205 A * | 10/1962 | Ennor | ........................ | 433/35 |
| 3,468,029 A * | 9/1969 | Moore | ........................ | 433/38 |
| 3,527,219 A * | 9/1970 | Greenberg | ........................ | 433/25 |
| 3,765,092 A * | 10/1973 | Neuwirth | ........................ | 433/47 |
| 3,882,601 A * | 5/1975 | Jahn | ........................ | 433/214 |
| 4,401,616 A * | 8/1983 | Wagner | ........................ | 264/138 |
| 4,450,122 A * | 5/1984 | Gallina | ........................ | 264/46.6 |
| 4,521,171 A * | 6/1985 | Noonan, Jr. | ........................ | 425/2 |
| 4,553,936 A * | 11/1985 | Wang | ........................ | 433/37 |
| 4,867,680 A * | 9/1989 | Hare et al. | ........................ | 433/37 |
| 5,520,539 A * | 5/1996 | Divjak | ........................ | 433/37 |
| 5,593,699 A * | 1/1997 | Grassi | ........................ | 425/2 |
| 5,755,233 A * | 5/1998 | Adell | ........................ | 128/859 |
| 6,149,426 A * | 11/2000 | Singer et al. | ........................ | 433/37 |
| 6,247,926 B1 * | 6/2001 | Thornton | ........................ | 433/48 |
| 6,364,665 B1 * | 4/2002 | Trettenero | ........................ | 433/215 |
| 6,379,147 B1 * | 4/2002 | Georgakis et al. | ........................ | 433/37 |
| 6,848,905 B2 * | 2/2005 | Jacobs et al. | ........................ | 433/37 |
| 6,964,568 B1 * | 11/2005 | Segal | ........................ | 433/45 |
| 7,137,813 B1 * | 11/2006 | Roetzer | ........................ | 433/37 |
| 7,704,074 B2 * | 4/2010 | Jensen | ........................ | 433/37 |
| 2006/0172253 A1 * | 8/2006 | Pumphrey et al. | ........................ | 433/37 |
| 2006/0269904 A1 * | 11/2006 | Suchan et al. | ........................ | 433/213 |
| 2010/0035211 A1 * | 2/2010 | Monicelli | ........................ | 433/214 |

FOREIGN PATENT DOCUMENTS

WO    2006/069024 A2    6/2006

* cited by examiner

*Primary Examiner* — Todd Manahan
*Assistant Examiner* — Michael R Ballinger
(74) *Attorney, Agent, or Firm* — Lanier Ford Shaver & Payne, P.C.

(57) ABSTRACT

An apparatus of the present disclosure has a dental tray cup filled with a silicone elastomer and elastomeric sheeting covering the silicone elastomer in the dental tray cup. A method of the present disclosure comprises the steps of providing a dental tray, filling the dental tray with an elastomeric material, covering the elastomeric material in the dental tray with a sheeting.

14 Claims, 7 Drawing Sheets

CUSTOM FIT DENTAL TRAY AND METHOD FOR MAKING SAME

CROSS REFERENCE TO RELATED APPLICATIONS

This application claims priority to U.S. Provisional Patent Application Ser. No. 61/070,390, entitled "Custom Fit Dental Tray and Method for Making Same," filed on Mar. 21, 2008, U.S. Provisional Patent Application Ser. No. 61/123,123, entitled "Custom Fit Dental Tray and Method for Making Same," filed on Apr. 4, 2008, and U.S. Provisional Patent Application Ser. No. 61/099,235, entitled "Custom Fit Dental Tray and Method for Making Same," filed on Sep. 23, 2008, all which are fully incorporated herein by reference.

FIELD OF THE INVENTION

The present invention relates generally to the field of dentistry. In particular, the present invention relates to a custom fit dental tray and method for making same.

BACKGROUND OF THE INVENTION

In dentistry, impressions are oftentimes made of a patient's teeth. To make an impression of a patient's teeth, polyvinyl siloxane (PVS), a silicone elastomer, is poured into a cup of a dental impression tray. The dental impression tray is then pressed onto the patient's teeth, causing the PVS to ooze through a plurality of holes in the dental impression tray and an impression of the patient's teeth is made in the PVS as the residual PVS escapes.

The cup and PVS are then removed from the patient's teeth, and after some time the impression made of the patient's teeth in the PVC hardens. This hardened impression can then be used in various ways, including making dental trays.

To create custom fit dental trays from the hardened impressions, a technique using a vacuuforming machine is used to create the custom fit dental trays from a model made from the impressions. This process is time consuming and may not result in a custom fit dental tray having a uniform thickness.

Custom fit dental trays dental trays may also be made of ethylene-vinyl acetate (EVA) material and are created using a boil-and-bite method. Such boil-and-bite type trays are used in sports to protect teeth; however, the material that is used is very thick thereby limiting their utility.

Custom fit dental trays are used in a variety of ways. For example, custom fit dental trays are used for teeth bleaching, treatment of periodontal disease, desensitizing teeth, remineralizing teeth, treatment of tooth decalcification, breath freshening, root caries treatment, among others. Solutions of various chemical compositions are placed into the custom formed mouth tray and the tray is placed over the teeth of the user to allow such chemicals to have intimate contact with dental structures undiluted by oral fluids.

SUMMARY

An apparatus in accordance with an embodiment of the present disclosure comprises a dental tray cup filled with a silicone elastomer and elastomeric sheeting covering the silicone elastomer in the dental tray cup.

A method in accordance with an embodiment of the present disclosure comprises the steps of filling a dental tray with an elastomeric material, heating a sheeting of elastomeric material, and placing the heating sheeting over the elastomeric-filled dental tray. The method further comprises pressing the elastomeric-filled dental tray and sheeting over teeth, removing the tray and sheeting from the teeth, and removing the sheeting from the dental tray.

BRIEF DESCRIPTION OF THE DRAWINGS

The present invention is described with reference to the accompanying drawings. In the drawings, like reference numbers indicate identical or functionally similar elements. Additionally, the left-most digit(s) of a reference number identifies the drawing in which the reference number first appears.

DETAILED DESCRIPTION

Figure 1:
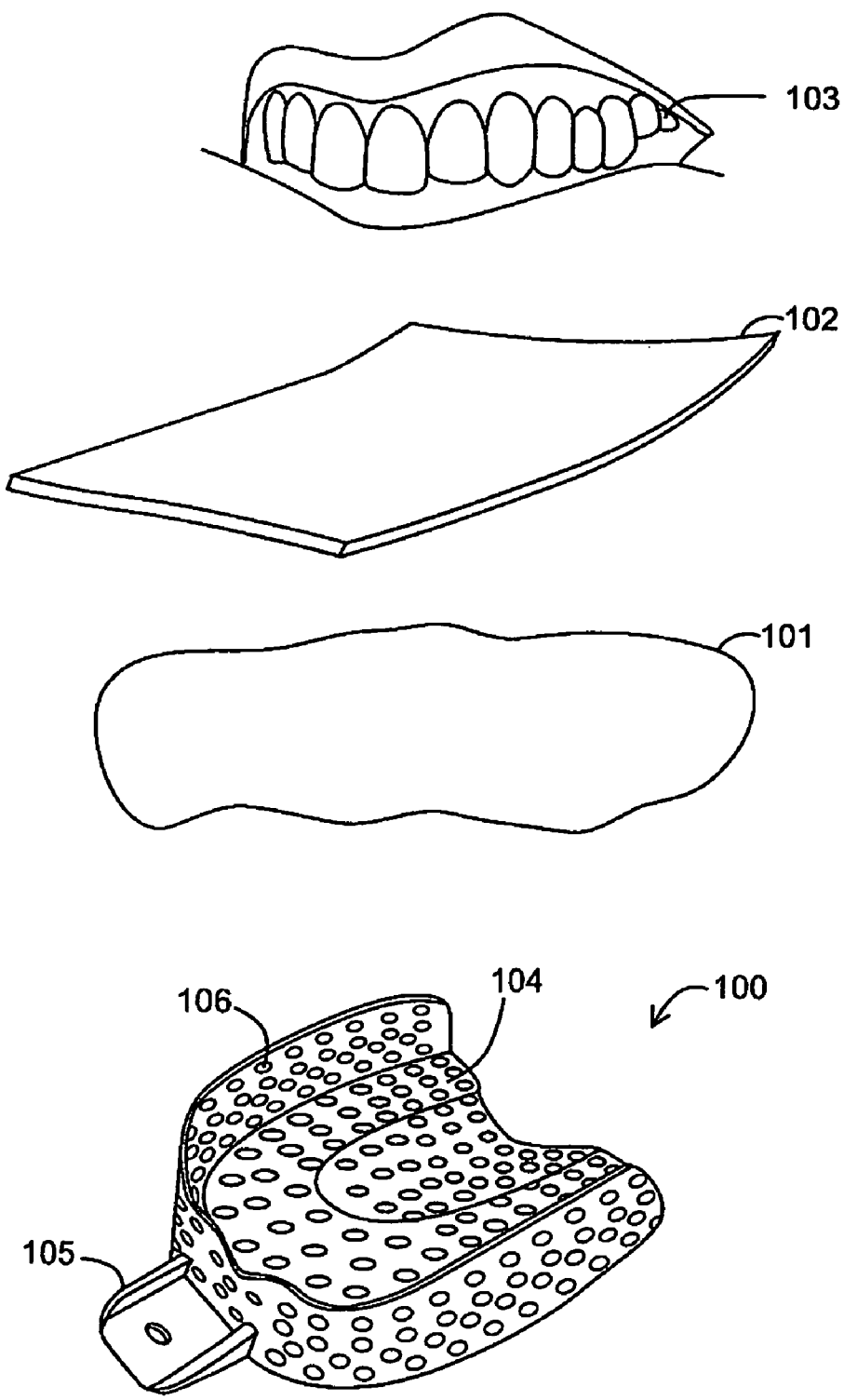
FIG. 1 is an exploded view of an exemplary apparatus in accordance with an embodiment of the present disclosure illustrating a method in accordance with an embodiment of the present disclosure.

FIG. 1 is an exploded view depicting an exemplary process for creating a custom dental tray (not shown) in accordance with an embodiment of the present disclosure. FIG. 1 depicts a dental impression tray 100, polyvinyl siloxane (PVS) 101, a sheeting 102 of ethylene-vinyl acetate (EVA), and a person's upper set of teeth 103.

The dental impression tray 100 comprises a cup 104 and a handle 105. Formed in the cup 104 is a plurality of openings 106. During the process, the cup 104 receives the PVS 101, and the openings 106 allow the PVS 101 to escape from the cup 104 when an impression is being made of a patient's teeth, which is illustrated further herein.

Note that the dental impression tray 100 can be various sizes, e.g., small, medium, and large. In addition, they may come in a maxillary and mandibular configuration. The size and type of the dental impression tray 100 used in the method described herein depends upon the size of the patient's mouth.

Further note that the sheeting 102 is comprised of EVA, which is the copolymer of ethylene and vinyl acetate. The sheeting 102 is a soft, flexible material, not unlike elastomeric materials. In one embodiment, the sheeting 102 is heat formable and exhibits a melting point compatible with a patient's temperature sensitivity. In such an embodiment, the sheeting 102 is molten at a temperature above body temperature but not so hot that it runs tissues. Thus, in such an embodiment the sheeting 102 melts between 100 and 180 degrees Fahrenheit or between 110 and 145 degrees Fahrenheit. Further, the sheeting 102 is between 0.030 and 0.040 inches in thickness.

Figure 2:
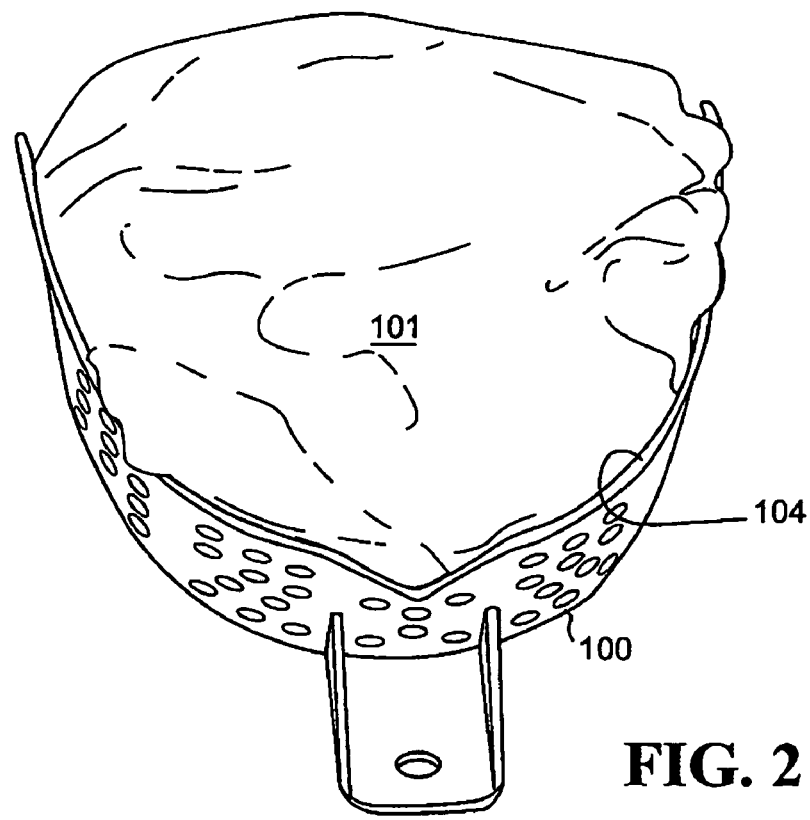
FIG. 2 is a dental impression tray of FIG. 1 filled with polyvinyl siloxane (PVS).

During the process of creating the custom dental tray, the PVS 101 is placed within the cup 104 of the dental impression tray 100. FIG. 2 depicts the dental impression tray 100 and the cup 104 filled with the PVS 101.

Figure 3:
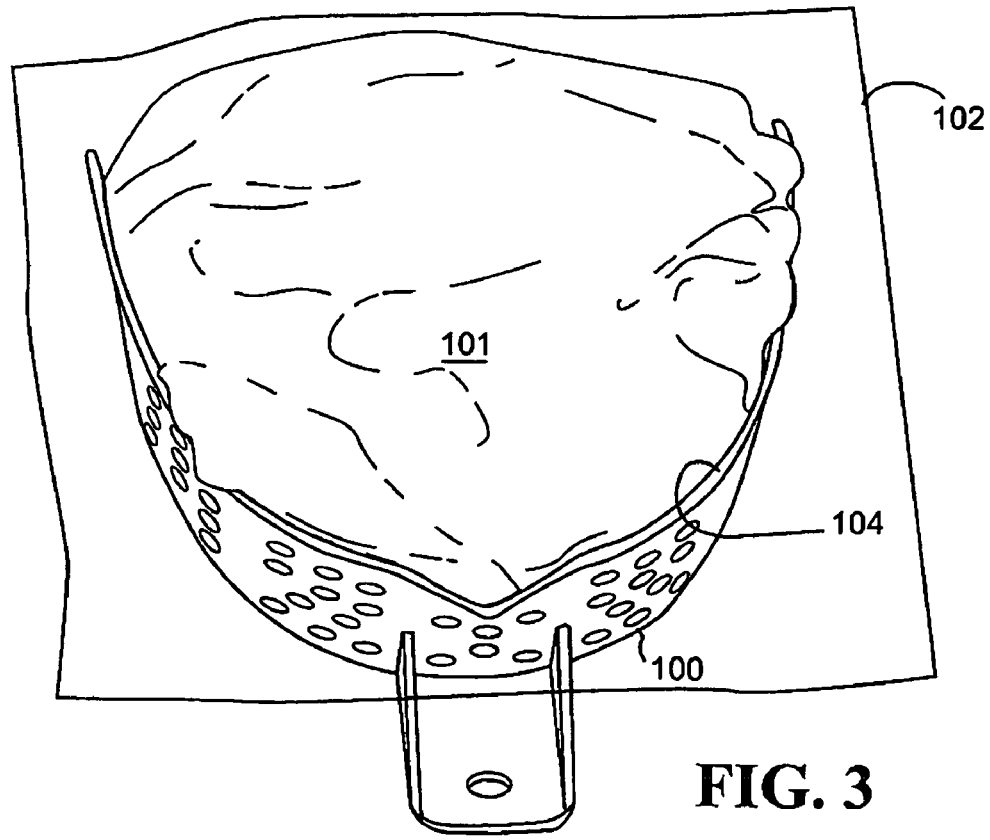
FIG. 3 depicts the dental impression tray of FIG. 2 filled with polyvinyl siloxane (PVS) and overlaid with a sheeting of ethylene-vinyl acetate (EVA).

The sheeting 102 is heated and is placed so as to overlay the PVS 101. FIG. 3 depicts the dental impression tray 100, the cup 104 filled with the PVS 101, and the PVS 101 overlaid with the heated sheeting 102.

With reference to FIG. 1, a user (not shown) grasps the handle 105 of the custom dental tray 100 that is filled with the PVS 101 and covered with the sheeting 102. The user presses the dental tray 100 against the teeth 103 such that the teeth 103 fit within the cup 104 of the dental impression tray 100.

In one embodiment, the sheeting 102, PVS 101, and the dental impression tray 100 may be sold as a unitary product, which is described further herein. In such an embodiment, the tray 100, the PVS 101, and the sheeting 102 may be heated as a unit, as depicted in FIG. 3. In another embodiment, the sheeting 102 may be separately heated so that it is deformable. The tray 100 may then be loaded with PVS 101, and the heated sheeting 102 placed over the PVS 101 prior to being placed and pressed over the teeth 103 (FIG. 1) as described.

Figure 4:
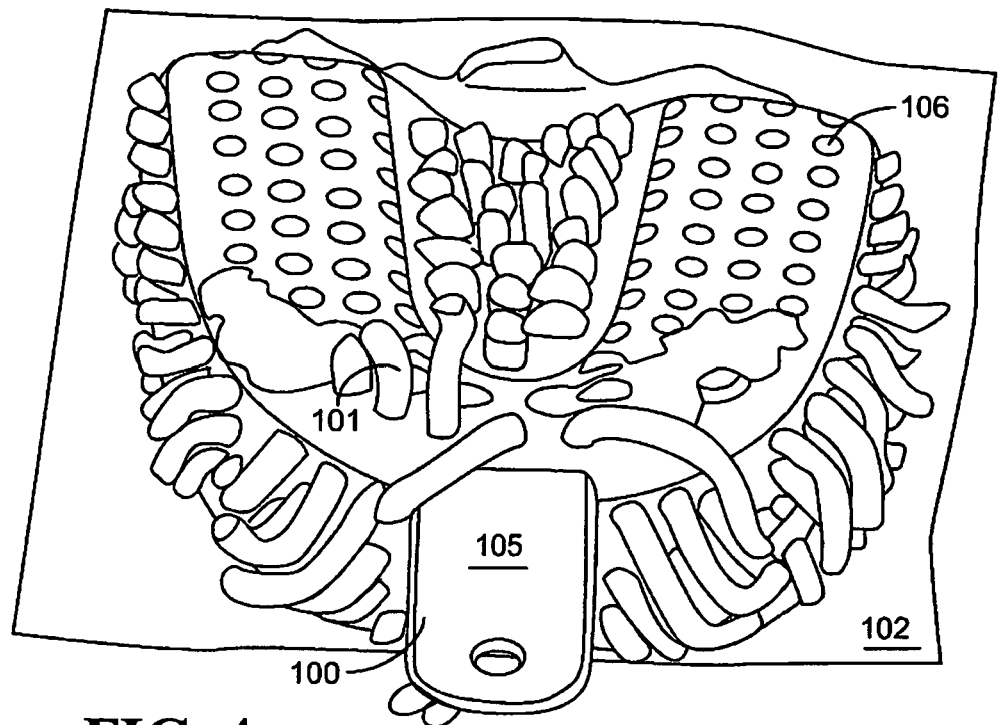
FIG. 4 is a bottom view of the dental tray of FIG. 1 after an impression has been made in the sheeting.

FIG. 4 depicts a bottom view of the dental impression tray 100 after the dental impression tray 100 has been firmly pressed against the teeth 103 (FIG. 1). As the tray 100 is being pressed against the teeth 103, the sheeting 102 deforms to the topography of the teeth 103, which is described further with reference to FIG. 5. Further, as the dental tray 100 is pressed against the teeth 103, excess PVS 101 escapes from the cup 104 (FIG. 1) of the dental impression tray 100 through the openings 106 as the sheeting 102 deforms.

Figure 5:
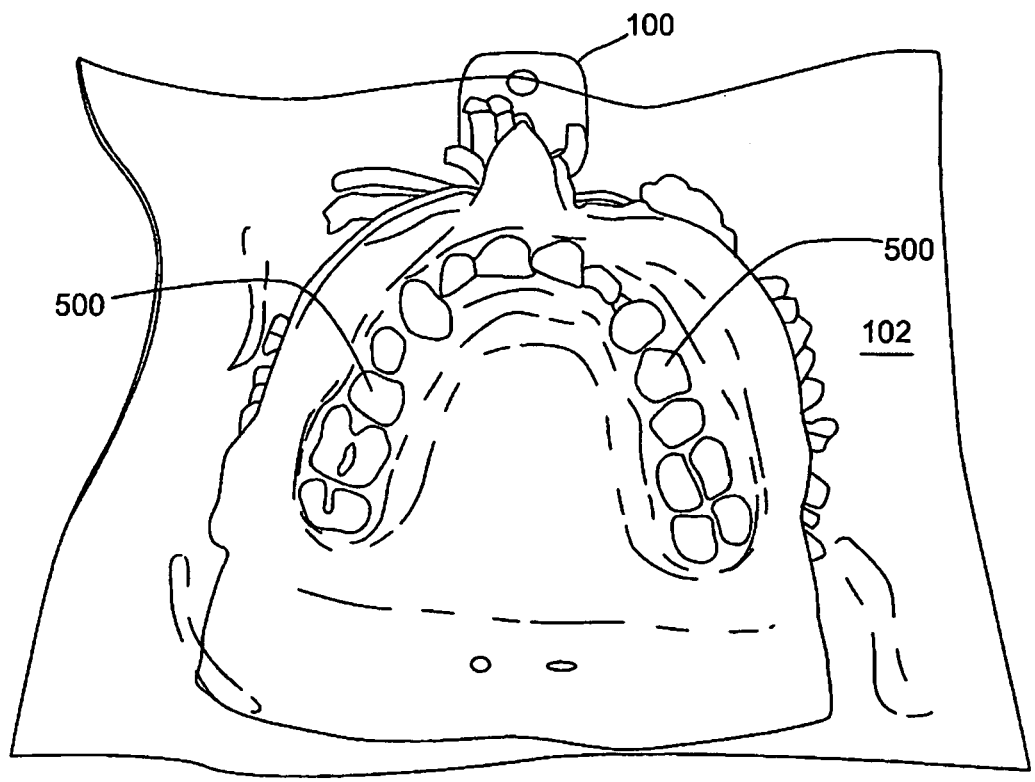
FIG. 5 is a top view of the dental tray of FIG. 1 after an impression has been made in the sheeting.

FIG. 5 depicts a top view of the dental impression tray 100 after the dental impression tray 100 has been firmly pressed against the teeth 103 (FIG. 1) and removed from the teeth 103. In FIG. 5, the tray 100 filled with the PVS 101 that is overlaid with the sheeting 102 is depicted so that the sheeting 102 is shown as the front layer.

Once the dental impression tray 100 is removed from the teeth 103, an impression 500 has been formed in the sheeting 102. In this regard, the heated sheeting 102 deforms corresponding to the topography of the teeth 103 thereby creating the impression 500 of the patient's teeth 103 in the sheeting 102.

Note that the sheeting 102 can be heated in any suitable manner now known or future-developed. As examples, an electric heating element, boiling water, hot air blower or any other means may be used to bring the temperature of the sheeting 102 to a melting point, yet keep it below the temperature that would cause tissue damage or discomfort for the patient.

Figure 6:
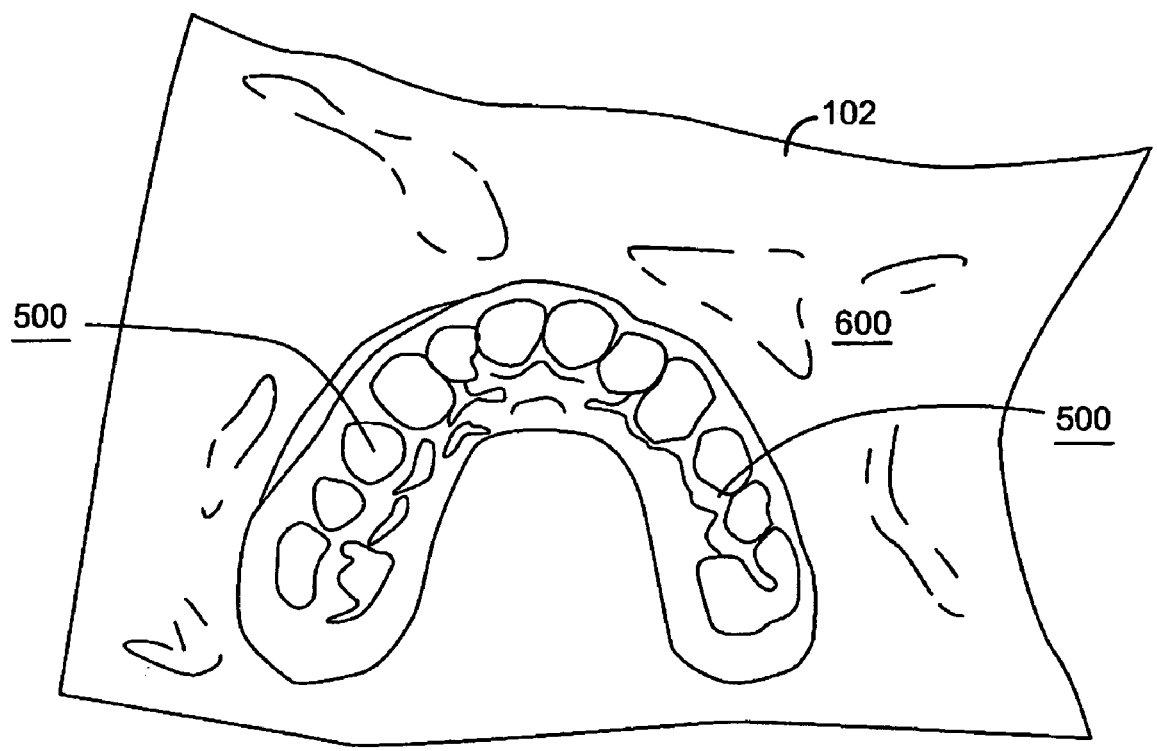
FIG. 6 depicts the sheeting after it has been removed from the PVS-filled dental tray depicted in FIG. 5.

FIG. 6 depicts the sheeting 102 after the sheeting 102 has been removed from the PVS 101 (FIG. 1) and the tray 100 (FIG. 1). Once the sheeting 102 is removed, it retains the impression 500 of the teeth 103 (FIG. 1). Around the impression 500 is excess sheeting 600. This excess sheeting 600 can be cut away, for example with a pair of scissors (not shown).

Figure 7:
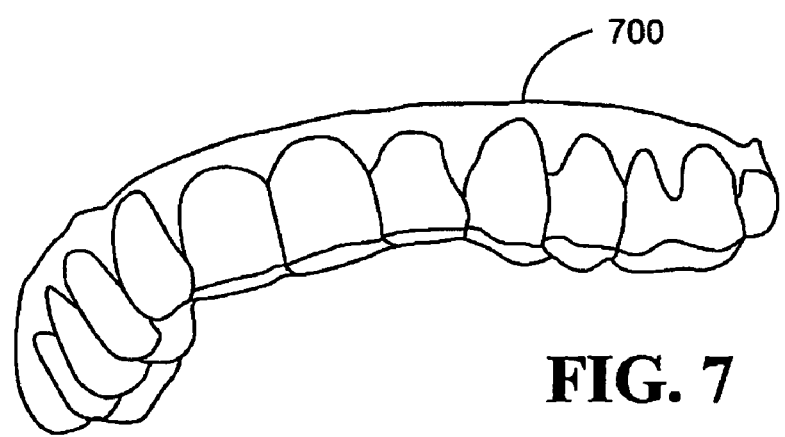
FIG. 7 depicts a custom fit dental tray after excess sheeting has been removed from the sheeting of FIG. 6.

FIG. 7 depicts a custom fit dental tray 700 formed when the excess sheeting 600 (FIG. 6) is cut away from the impression 500 (FIG. 6). Note that the excess sheeting 600 may be cut away in a variety of configurations depending upon the final use. For example, the excess sheeting 600 may be trimmed away from the impression 500, as shown, thereby leaving the custom dental tray 700. In addition, however, the excess sheeting 600 may also be trimmed at the margin of the teeth 103 (FIG. 1) and gingival tissues (not shown) such that the finished tray 700 touches the gingival tissues.

Note that the tray 700 has a uniform thickness, and the tray 700 is fabricated within the mouth of the patient with one sitting technique that equals or exceeds a laboratory fabricated custom molded tray that requires much more time and expense to produce. Further note that the rigid impression tray 100 and the PVS 101 provide support for the soft molten sheeting 102 that is overlaid on the PVS 101.

Figure 8:
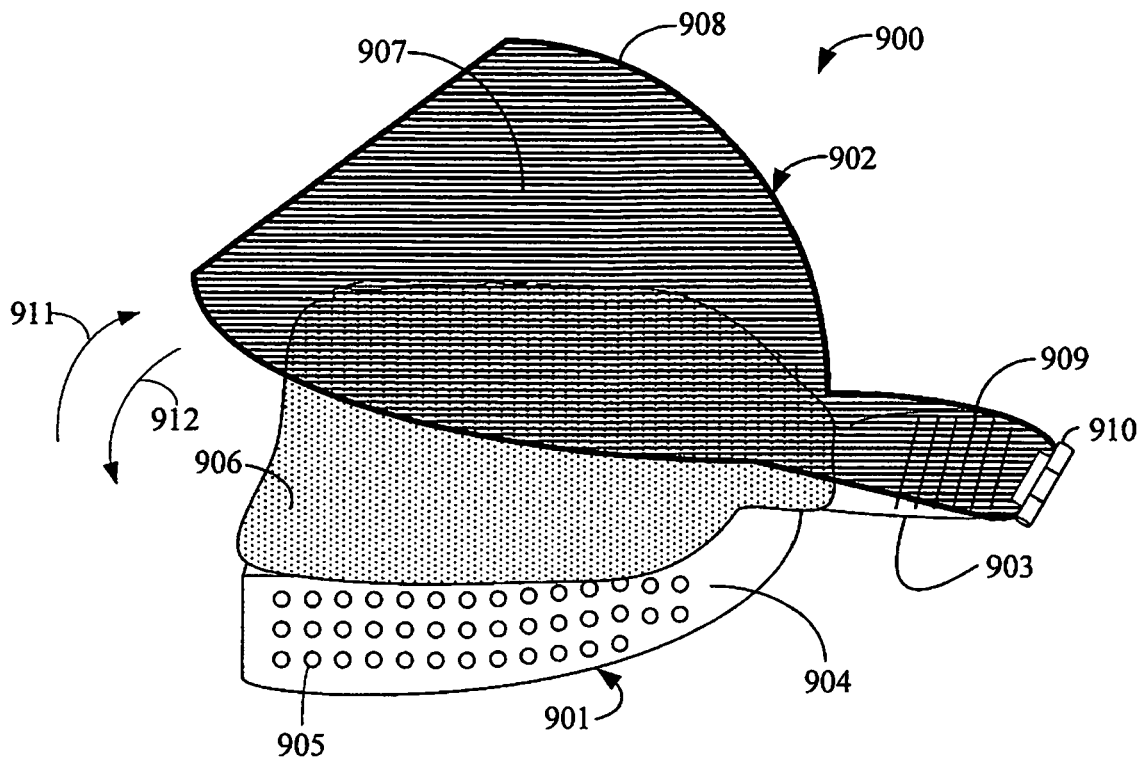
FIG. 8 is an exemplary hinged dental tray in accordance with another embodiment of the present disclosure shown in an open position.

FIG. 8 is a perspective view of an EVA-hinged dental tray 900 in accordance with an embodiment of the present disclosure. The dental tray 900 comprises an impression tray 901 and a hinged upper component 902. The impression tray 901 comprises a handle 903 and a cup 904. A plurality of openings 905 are formed in the cup 904.

The openings 905 allow putty material 906, e.g., polyvinyl siloxane (PVS), to escape from the cup 904 when an impression is being made of a patient's teeth (not shown). The impression tray 904 can be various sizes, e.g., small, medium, and large. In addition, they may come in a maxillary and mandibular configuration. The size and type of the dental impression tray 904 used in the process described herein depends upon the size of the patient's mouth.

The hinged component 902 comprises a sheeting 907 of a polymer material, e.g., ethylene-vinyl acetate (EVA). Note that EVA is the copolymer of ethylene and vinyl acetate, as described hereinabove.

In one embodiment, the sheeting 907 is rigid such that the sheeting 907 is hingedly coupled to the handle 903 of the impression tray 904. The hinged component 902 further comprises a wire frame 908, and the sheeting 907 is affixed to the wire frame 908. In such an embodiment, the hinged wire frame 908 forms a handle 909, and the handle 909 is hingedly coupled to the handle 903 of the impression tray 901 via a hinge mechanism 910. The hinge mechanism 910 can be a type of hinge known in the art or future-developed. As examples, the hinge mechanism 910 may be a butt hinge or a butterfly hinge.

Note that the wire frame 908 is shown in the exemplary embodiment in FIG. 8. However, in other embodiments, the wire frame 908 may not be necessary. As an example, the sheeting 907 may consist of a material that is rigid such that the handle 909 can be directly coupled to the handle 903 without the presence of the wire frame 908.

A user (not shown) actuates the hinge mechanism 910 such that the hinged component 902 pivots about the hinge mechanism 910 in a direction indicated by reference arrow 911. Note that FIG. 8 depicts the dental tray 900 in an open position. The term "open position" refers to when the hinged component 902 is separated from the PVA-filled impression tray 901. When the dental tray 900 is in the open position, the sheeting 907 can be heated on both sides. When the dental tray 900 is in the open position, the sheeting 907 can be heated with hot air and/or hot liquid.

Figure 9:
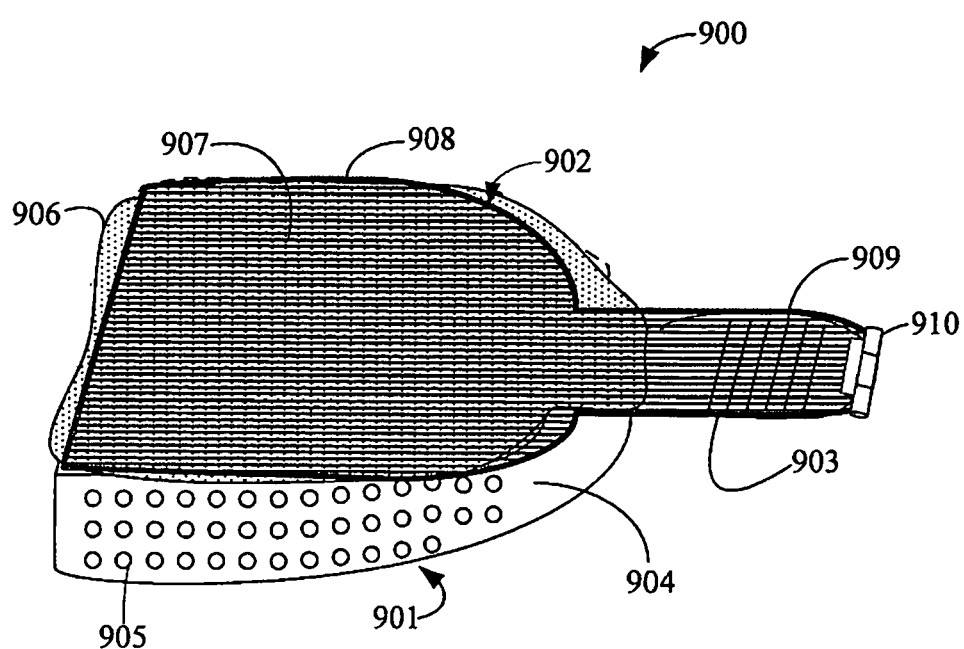
FIG. 9 is the hinged dental tray of FIG. 9 shown in a closed position.

Once the sheeting 907 has been heated, the user actuates the hinge mechanism 910 in a direction indicated by reference arrow 912 such that the hinged component 902 is in a closed position, as depicted in FIG. 9. The term "closed position" refers to that position of the dental tray 900 such that the dental tray 900 can be inserted into a patient's mouth (not shown) and an impression made of the patient's teeth (not shown).

Moving the hinged component 910 in the direction of reference arrow 912 to the closed position as depicted in FIG. 2, places the sheeting 907 over the putty material 906 that is filled in the cup 904 of the dental impression tray 901. Once the sheeting 907 is placed over the putty material 906, the dental tray 900 can be placed in the patient's mouth and an impression made of the patient's teeth, such as described with reference to FIG. 1.

Figure 10:
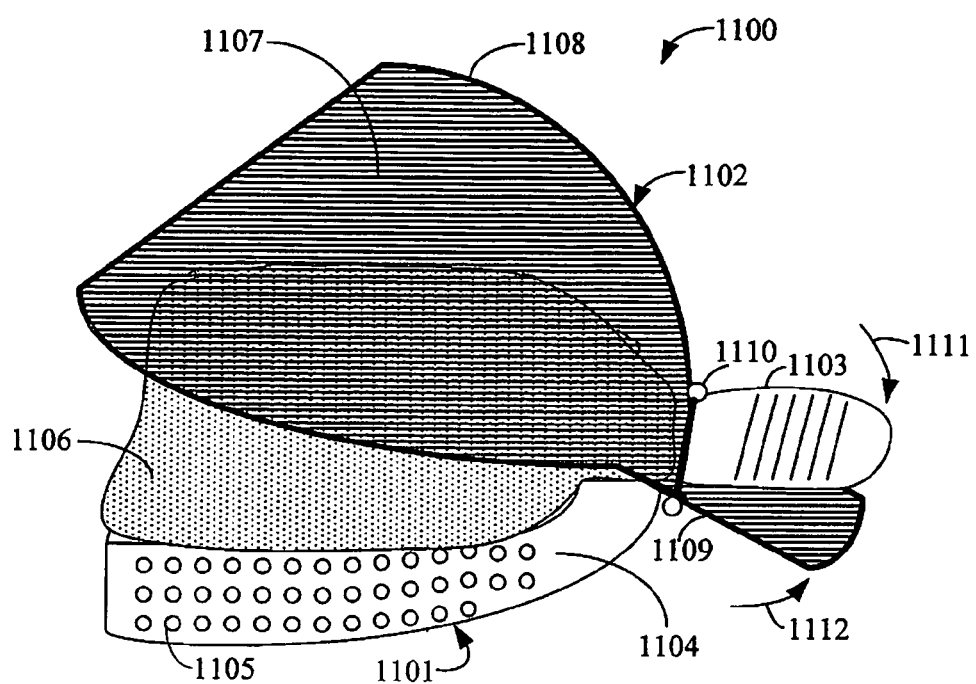
FIG. 10 is an exemplary hinged dental tray in accordance with another embodiment of the present disclosure shown in an open position.

FIG. 10 is a perspective view of an EVA-hinged dental tray 1100 in accordance with another embodiment of the present disclosure. The EVA-hinged dental tray 1100 is substantially similar to the EVA-hinged dental tray 900 depicted in FIG. 9 and described herein.

In this regard, the dental tray 1100 comprises an impression tray 1101 and a hinged upper component 1102. The impression tray 1101 comprises a handle 1103 and a cup 1104. A plurality of openings 1105 are formed in the cup 1104.

The hinged component I 102 comprises a sheeting 1107 of a polymer material, e.g., EVA. The hinged component 1102 further comprises a wire frame 1108, and the sheeting 1107 is affixed to the wire frame 1108. In such an embodiment, the hinged wire frame 1108 forms a handle 1109.

Note that the wire frame 1108 is shown in the exemplary embodiment in FIG. 10. However, in other embodiments, the wire frame 1108 may not be utilized. As an example, the sheeting 1107 may consist of a material that is rigid such that the handle 1109 can be directly coupled to the handle 1103 without the presence of the wire frame 908.

Figure 11:
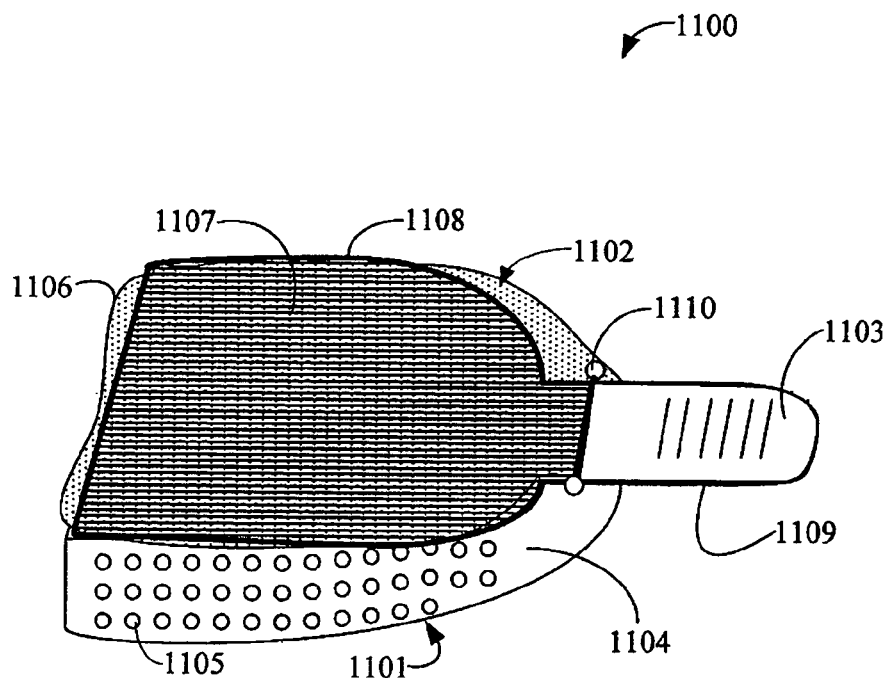
FIG. 11 is the hinged dental tray of FIG. 11 shown in a closed position.

In the embodiment depicted in FIG. 11, the handles 1103 and 1109 are transversely connected via a hinge pin 1110. Note that FIG. 11 depicts the dental tray 1100 in an open position. "Open position" refers to when the hinged component 1102 is separated from the PVA-filled impression tray 1101 by separating the handles 1103 and 1109 in directions indicated by reference arrows 1111 and 1112, respectively. When the dental tray 1100 is in the open position, the sheeting 12 can be heated on both sides by submerging the sheeting 1107 in a hot air or hot liquid chamber (not pictured).

Figure 12:
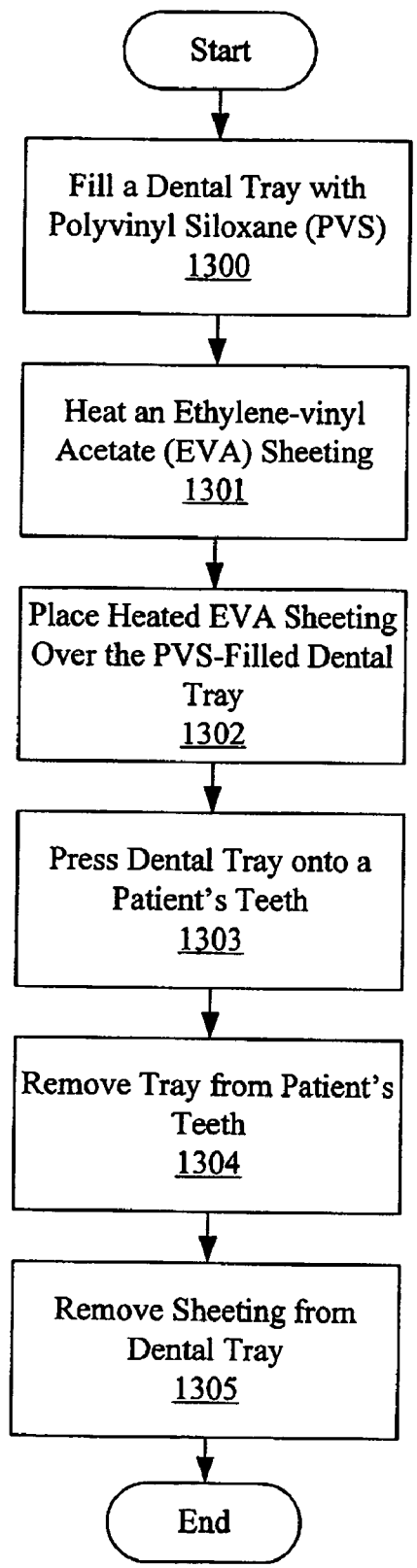
FIG. 12 is a flowchart depicting an exemplary method for making a custom fit dental tray in accordance with an embodiment of the present disclosure.

In order to close the dental tray 1100, the user releases the handles 1103 and 1109 and the hinge pin 1110 forces the handles 1103 and 1109 together, thereby leaving the dental tray 1100 in a closed position, as depicted in FIG. 12. The "closed position" refers to that position of the dental tray 1100 such that the dental tray 1100 can be inserted into a patient's mouth (not shown) and an impression made of the patient's teeth (not shown) on the sheeting 1107.

Releasing the hinge pin 1110 so that the dental tray 1100 is in the closed position as depicted in FIG. 11, places the sheeting 1107 over the putty material 1106 that is filled in the cup 1104 of the dental impression tray 1101. Once the sheeting 1107 is placed over the putty material 1106, the dental tray 1100 can be placed in the patient's mouth and an impression made of the patient's teeth in the Sheeting 1107.

FIG. 12 depicts an exemplary method in accordance with an embodiment of the present disclosure.

In step 1300, a user (not shown) fills a dental impression tray 100 (FIG. 1) with PVS 101 (FIG. 1). In step 1301, the user heats a sheeting 102 (FIG. 1). Heating can be done in a variety of ways as described herein.

In step 1302, the user places the heated sheeting 102 over the PVS-filled dental impression tray 100. In step 1303, the user presses the sheeting 102 over a patient's teeth 103 (FIG. 1). After some time, the user removes the tray 100 with the sheeting 102 from the patient's teeth, in step 1304. In step 1305, the user removes the sheeting 102 now exhibiting an impression 500 (FIG. 5) from the PVS-filled dental impression tray 100, thereby forming a custom fit dental tray 700 (FIG. 7) fit for the patient's teeth.

Note that the excess EVA 600 (FIG. 6) may be removed with scissors, as described with reference to FIG. 6. How much of the excess is removed depends upon how the custom fit dental tray 700 is intended to be used.

What is claimed is:

1. An apparatus, comprising:
   a dental tray cup filled with a silicone elastomer;
   a sheeting covering the silicone elastomer in the dental tray cup, wherein the dental tray cup comprises a handle, wherein the sheeting comprises a handle, and wherein the dental tray cup handle is hingedly coupled to the sheeting handle.

2. The apparatus of claim 1, wherein the sheeting comprises ethylene-vinyl acetate.

3. The apparatus of claim 1, wherein the silicone elastomer consists of polyvinyl siloxane.

4. A method, comprising:
   providing a dental tray;
   filling the dental tray with an elastomeric material; and
   covering the elastomeric material in the dental tray with a sheeting, wherein the dental tray comprises a handle, wherein the sheeting comprises a handle, and wherein the dental handle is hingedly coupled to the sheeting handle.

5. The method of claim 4, wherein the sheeting consists of ethylene-vinyl acetate.

6. The method of claim 5, further comprising the step of heating the sheeting.

7. The method of claim 6, further comprising the step of placing the heated sheeting over the elastomeric-filled dental tray.

8. The method of claim 4, further comprising the step of pressing the elastomeric-filled dental tray and sheeting over teeth.

9. The method of claim 8, further comprising the step of removing the tray and sheeting from the teeth.

10. The method of claim 9, further comprising the step of removing the sheeting from the dental tray.

11. The method of claim 10, further comprising the step of trimming excess sheeting from the sheeting to create a custom fit dental tray.

12. The method of claim 4, further comprising:
   hingedly separating the sheeting from the elastomeric material; and
   heating the sheeting when the sheeting is hingedly separated from the elastomeric material.

13. The method of claim 12, further comprising:
   hingedly closing the heated sheeting so that the heated sheeting rests on the elastomeric material.

14. The method of claim 13, further comprising:
   inserting the dental tray and the heated sheeting in a patient's mouth; and
   pressing the dental tray and the heated sheeting against teeth in the patient's mouth.

* * * * *